United States Patent [19]

Gay et al.

[11] 4,254,265
[45] Mar. 3, 1981

[54] SELECTED 5-TRICHLOROMETHYLTHIOAMINO DERIVATIVES OF 3-TRIHALOMETHYL-1,2,4-THIADIAZOLE AND THEIR USE AS FUNGICIDES

[75] Inventors: Walter A. Gay, Cheshire; Elizabeth A. Twohig, Seymour, both of Conn.

[73] Assignee: Olin Corporation, New Haven, Conn.

[21] Appl. No.: 142,201

[22] Filed: Apr. 21, 1980

[51] Int. Cl.³ .................. A01N 43/82; C07D 285/08
[52] U.S. Cl. ..................................... 548/128; 424/270
[58] Field of Search ........................................ 548/128

[56] References Cited

U.S. PATENT DOCUMENTS

| | | | |
|---|---|---|---|
| 3,260,588 | 7/1966 | Schroeder | 71/90 |
| 3,260,725 | 7/1966 | Schroeder | 548/128 |
| 3,324,141 | 6/1967 | Bernstein | 548/128 |
| 3,720,684 | 3/1973 | Krenzer et al. | 548/128 |
| 3,764,685 | 10/1973 | Krenzer et al. | 424/270 |
| 3,993,693 | 11/1976 | Bhutani | 260/543 H |

Primary Examiner—Alton D. Rollins
Attorney, Agent, or Firm—William A. Simons; Thomas P. O'Day

[57] ABSTRACT

Disclosed are selected 5-trichloromethylthioamino derivatives of 3-trihalomethyl-1,2,4-thiadiazole compounds which have the formula:

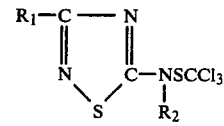

wherein $R_1$ is $CCl_3$ or $CF_3$; and wherein $R_2$ is hydrogen, a lower alkyl having 1 to 4 carbon atoms, phenyl and substituted phenyl wherein said substituents are lower alkyl having 1 to 4 carbon atoms, lower alkoxy having 1 to 4 carbon atoms, amino, nitro, halo and mixtures thereof. These compounds are diclosed to be agricultural fungicides.

5 Claims, No Drawings

SELECTED 5-TRICHLOROMETHYLTHIOAMINO DERIVATIVES OF 3-TRIHALOMETHYL-1,2,4-THIADIAZOLE AND THEIR USE AS FUNGICIDES

BACKGROUND OF THE INVENTION

1. Field of the Invention

This invention relates to selected 5-trichloromethyl-thioamino derivatives of 3-trihalomethyl-1,2,4-thiadiazole compounds and their use as fungicides.

2. Description of the Prior Art

Various 3,5-substituted-1,2,4-thiadiazole compounds are known to possess different types of agricultural pesticidal activity. For example, U.S. Pat. Nos. 3,260,588 and 3,260,575, which issued to H. Schroeder on July 12, 1966 disclose that certain 3-trichloromethyl-5-substituted-1,2,4-thiadiazoles are effective fugicides. Furthermore, U.S. Pat Nos. 3,720,684 and 3,764,685, which issued to J. Krenzer and S. Richter on Mar. 13, 1973 and Oct. 9, 1973, respectively, suggest that 3-trichloromethylmercaptoamino-5-chloro-1,2,4-thiadiazole is an effective fungicide.

BRIEF SUMMARY OF THE INVENTION

Accordingly, the present invention is directed to, as compositions of matter, selected 5-trichloromethyl-thioamino derivatives of 3-trihalomethyl-1,2,4-thiadiazole which have the formula:

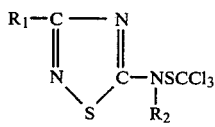

wherein $R_1$ is $CCl_3$ or $CF_3$; and wherein $R_2$ is hydrogen, lower alkyl having 1 to 4 carbon atoms, phenyl and substituted phenyl wherein ring substituents are lower alkyl have to 4 carbon atoms, lower alkoxy having 1 to 4 carbon atoms, amino, nitro, halo and mixtures thereof. The present invention is also directed to the use of these compounds as fungicides.

DETAILED DESCRIPTION

The 5-trichloromethylthioamino derivatives of the present invention may be prepared by reacting the corresponding 5-amino-(or substituted amino)-3-trihalomethyl-1,2,4-thiadiazole with trichlloromethanesulfenyl chlorde in the presence of a suitable solvent with or without base as an acid acceptor. This general reaction is illustrated in Equation A below. In equation (A), 5-amino-3-trichloromethyl-1,2,4-thiadiazole is reacted with trichloromethanesulfenyl in the presence of the base, triethylamine, in order to prepare 5-trichloromethylthioamino-3-trichloromethyl-1,2,4-thiadiazole:

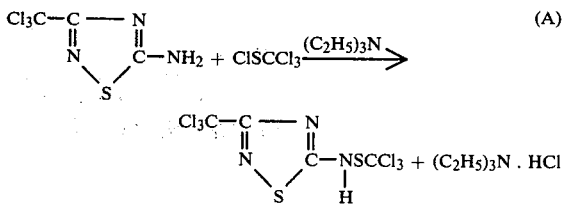

Suitable 5-amino substituent-3-trihalomethyl-1,2,4-thiadiazole reactants include, besides 5amino-3-trichloromethyl-1,2,4-thiadiazole, 5methylamino-3-trichloromethyl-1,2,4-thiadiazole, 5-phenylamino-3-trichloromethyl-1,2,4-thiadiazole, and 5-amino-3-triflurormethyl-1,2,4-thiadiazol trifluoromethyl-1,2,4thiadiazole and the like. 5-Amino-3trichloromethyl-1,2,4-thiadiazole and 5methylamino-3-trifluoromethyl-1,2,3-thiadiazole are both described in U.S. Pat. Nos. 3,260,588 and 3,260,725, and are made by reacting 5-chloro-3-trichloromethyl-1,2,4-thiadiazole with ammonia or methylamine, respectively. 5-Amino-3-trifluoromethyl-1,2,4-thiadiazole is described in U.S. Pat. No. 3,917,478, which issued to Moser et al on Nov. 4, 1975, and is prepared by (1) the side-chain fluorination of 5-chloro-3-trichloromethyl-1,2,4-thiadiaxole with a Swart's fluorination mixture consisting of antimony trifluoride, antimony trichloride and chlorine, followed by (2) ammoniation of 5-chloro-3-trifluoromethyl-1,2,4-thiadiazole.

Trichloromethanesulfenyl chloride is a commercially available reagent made by the chlorination of carbon disulfide. U.S. Pat. No. 3,993,693, which issued to S. Bhutani on July 30, 1975, teaches one method for preparing this compound.

Any conventional reaction conditions designed to produce a reaction between the amines and the sulfenyl chloride may be employed in the synthesis of the present compounds and thus the present invention is not intended to be limited to any particular reaction conditions. Advantageously and preferably, the reactions are performed with equimolar quantities of the reactants in the presence of a suitable inert solvent. An aromatic solvent such as benzene or xylene is a preferred solvent but other inert solvents, such as dioxane, may be used. The reaction temperature and time will both depend upon many factors, including the specific reactants used. In most situations from about 50° to 150° C. and reaction times from 1 to 48 hours may be preferred. The product may be recovered from the reaction mixture by any conventional means, for example, extraction, trituration, and the like. Finally, it should be noted that while the reaction illustrated in Equation A is a preferred method of preparing compounds of the present invention, other synthesis methods my be employed.

Representative 5-trichloromethylthioamino derivatives of the present invention include the 3-trichloromethyl- or 3-trifluoromethyl-1,2,4-thiadiazoles having the following 5-substituents:

5-trichloromethylthioamino-
5-(N-methyl-trichloromethylthioamino)-
5-(N-phenyl-trichloromethylthioamino)-
5-[N-(o-tolyl)-trichloromethylthioamino]-
5-[N-(4-chlorophenyl)-3trichloromethylthioamino]-
5-[N-(4-methoxyphenyl)-3-trichloromethylthioamino]-
5-[N-(3-nitrophenyl)-3-trichloromethylthioamino]-
5-[N-(4-aminophenyl)-3-trichloromethylthioamino]-
5-[N-(2,4dichlorophenyl)-trichloromethylthioamino]-

Also, in accordane with the present invention, it has been found that the compounds of Formula I, above, may be utilized as effective foliar fungicides. In practicing the process of the present invention, fungi are contacted with a fungicidally effective amount of one or more of these compounds. It is to be understood that the term "fungicidally effective amount" as used in the specification and claims herein is intended to include any amount that will kill or control said foliar fungi when either employed by itself (i.e., in full concentration) or in sufficient concentrations with a carrier or other substance. Of course, this amount may be constantly changing because of the possible variations in many parameters. Some of these may include: the number and type of fungi to be controlled or killed; the type of media to which the present compound can be applied (e.g., seedlings or fully grown plants); degree of effectiveness required; and type of carrier, if any. Generally speaking, applications of an aqueous spray containing at least about 5, more preferably in the range of about 30 to 300, parts per million of the chemical of the present invention may give satisfactory fungi control.

This step of contracting may be accomplished by applying this compound to the fungi themselves, their habitat, dietary media such as vegetation, crops and the like, including many which these pests may attack.

The above-mentioned compounds of the present invention may be formulated and applied by any conventional methods that include using the compound alone or with a carrier or other substances which may enhance the effectiveness of the chemical or facilitate handling. Moreover, the activity of the present compound may be broadened by the addition thereto of other known pesticides such as other fungicides, herbicides, insecticides and the like.

Specific methods of formulating and applying these active compounds include applying them in the form of dusts, dust or emulsion concentrates, wettable powders and concentrates, granulates, dispersions, sprays, solutions and the like.

The dusts are usually prepared by simply grinding together from about 1% to about 15% by weight of the active compound with a finely divided inert diluent such as walnut flour, diatomaceous earth, fullers earth, attaclay, talc or kaolin. Dust concentrates are made in similar fashion excepting that about 16% to about 75% by weight of active compound is ground usually together with the diluent. In practice, dust concentrates are then generally admixed at the site of use with more inert diluent before it is applied to the plant foliage, soil, or animals which are to be protected from fungi attack.

Wettable powders are generally prepared in the same manner as dust concentrates, but usually about 1% to about 10% by weight of a dispersng agent, for example. an alkali metal lignosulfonate and about 1% to about 10% of a surfactant, such as a non-ionic surfactant, are incorporated in the formulation. For application to agronomic crops, shrubs, ornamentals and the like, the wettable powder is usually dispersed in water and applied as a spray.

Emulsifiable liquids may be prepared by dissolving the active compound in an organic solvent, such as xylene or acetone, and admixing the thus formed solution with a surfactant or an emulsifier. The emulsified liquid is then generally dispersed in water for spray or dip application.

It is possible to formulate granulates whereby the active compound is dissolved in an organic solvent and the resulting solution is then applied to a granulated mineral or the like (e.g., bentonite, $SiO_2$, or the like) followed by evaporating off the organic solvent. Granulates can also be obtained by the compacting of the carrier material with the active substance and then reducing this compacted material in size.

Furthermore, the applied formulations of the present invention include other liquid preparations such as dispersions, sprays or solutions. For these purposes, the above-mentioned active compound is normally dissolved in a suitable organic solvent, solvent mixtures or water. As organic solvents, it is possible to use any suitable aliphatic and aromatic hydrocarbon or their derivatives. It is preferred that the solvent be odorless and moreover, be inert to the active compound.

It should be clearly understood that the fungicide formulations, the ingrediens which may make up such formulations other than the active compound, the dosages of these ingredients, and means of applying thse formulations may include all known and conventional substances, amounts and means, respectively, that are suitable for obtaining the desired fungicidal result. And, therefore, such process parameters are not critical to the present invention.

Fungicides of the present invention may be effective for the control of the broad class of foliar fungi. Specific illustrations of foliar fungi wherein fungicidal activity has been shown include bean rust and cucumber anthracnose.

The following examples further illustrate the present invention. All parts and percentages employed therein are by weight unless otherwise indicated. Yields given are percent molar yields.

EXAMPLE 1

5-Trichloromethylthioamino-3-Trichloromethyl-1,2,4Thiadiazole

To a 3-neck flask equipped with condenser, thermometer, and stirring bar was added 11.7 g (0.05 mole) 5-amino-3trichloromethyl-1,2,4-thiadiazole, 5.1 g (0.05 mole) triethylamine and 150 milliliters of benzene. After 9.3 g (0.05 mole) trichloromethane-sulfenyl chloride was added, the reaction mixture was heated at reflux for 16 hours and filtered hot. The filtrate was evaporatd under vacuum to give an orange paste which was triturated with acetonitrile, filered and washed with petroleum ether to obtain 4.4 g (24% yield) of product; mp=180° C.

Analysis—Calculated for $C_4HCl_6N_3S_2$— C, 13.06%; H, 0.27%; Cl, 57.82%; N, 11.42%, S, 17.43%. Found: C, 13.34%; H, <0.27%; Cl, 58.02%; N, 11.60%; S, 17.14%.

EXAMPLE 2

5-(N-Methyl-Trichloromethylthioamino)-3-Trichloromethyl-1,2,4-Thiadiazole

To a 3-neck flask equpped with condenser, thermometer and stirring bar was added 11.6 g (0.05 mole) 5-methylamino-3-trichloromethyl-1,2,4- thiadiazole, 5.1 g (0.05 mole) triethylamine and 150 milliliters of benzene. After 9.3 g (0.05 mole) trichloromethane-sulfenyl chloride was added, the reaction mixture was heated at reflux for 20 hours and filtered hot. The filtrate was evaporated under vacuum to give a beige solid which was refluxed in 400 milliliters of ligroin and filtered. The ligroin was cooled, filtered and the filtrate evaporated to 20 milliliters and filtered. The resulting solid was recrystallized again from ligroin to obtain 4.4 g (23% yield) of product; mp=106° C.

Analysis—Calculated for $C_5H_3N_3Cl_6S_2$— C, 15.72%; H, 0.79%; Cl, 55.69%; N, 11.00%; S, 16.79% Found: C, 15.61%; H, <0.79%; Cl, 55.50%, N, 11.25%; S, 16.45%.

Foliar Fungicide Screen

The active materials formed in Examples 1 and 2 were then tested for activity as effective fungicides.

a uniform aqueous dispersion of each chemical made in the above examples as first prepared. These dispersions were made by dissolving each chemical in a solution of acetone containing the surfactant TRITON Z-155[1] (500 parts per million). Next, this solution was diluted with water (1:9) to obtain a stock solution of 10% by volume acetone and 90% by volume water with 50 ppm TRITON X-155 and the test chemical contained therein. This stock solution was diluted further with water/acetone mix to provide the desired concentration of the test material, if required.

[1] Manufactured by Rohm and Haas of Phildaelphia, PA and is a polyether alcohol.

The aqueous solutions containing each chemical were applied to various plants according to the methods stated below. These tests were designed to evaluate the ability of the chemical to protect non-infected foliage and eradicate recently established infection against major types of fungi such as rust and anthracnose that attack above-ground parts of plants.

Bean Rust

In primary screening, Pinto beans, which were in 2½ inch posts and 9 to 12 days old, were sprayed while rotating the plants on a turntable with an aqueous solution of each chemical of Examples 1 and 2. The aqueous solutions contained 260 parts per million of each active chemical. Simultaneously, the soil in each pot was drenched with aqueous solutions of each chemical in the amount of 25 lb./acre. After the spray deposit had dried, the plans were atomized with a suspension of uredospores [summer spore stage of bean rust (*Uromyces phaseoli*)] and placed in a moist chamber at 70° F. for 24 hours. After 7 days, the severity of pustule formation was rated on a scale of 0 (no inhibition) to10 (complete inhibition). See Table I foe the results of these tests.

In secondary screening, the same spraying and drenching procedures were followed, except lower concentrations were employed and the spraying and drenching was done separately. After each spraying or drenching, the plants were again atomized with a suspension of uredospores and tested for severity of pustule formation in the same manner. These resuls are also shown in Table I. The compound of Example 1 was not subjected to secondary screening against bean rust.

TABLE I

| | FUNGICIDAL ACTIVITY AGAINST BEAN RUST | | | | | | |
|---|---|---|---|---|---|---|---|
| | Primary screening | Secondary Screening | | | | | |
| Compound | 25 lb/acre drench & 260 ppm spray | 12.5 lb/acre drench | 6.3 lb/acre drench | 3.2 lb/acre drench | 130 ppm spray | 65 ppm spray | 33 ppm spray |
| Example 1 | 5 | — | — | — | — | — | — |
| Example 2 | 10 | 5 | 5 | 5 | 10 | 10 | 10 |

Cucumber Anthracnose

For the primary and secondary screening, two week old cucumber plants were atomized with a suspension of cucumber anthracnose spores (*Collectotrichium lagenarium*) and placed in a moist chamber at 70° F. for 24 hours. In the primary screening, the young plants were then sprayed while rotating the plants on a turntable with an aqueous solution that contained 260 parts per million by weight of the active chemicals of Examples 1 and 2. Simultaneously, the soil in each pot was drenched with aqueous dispersions of each chemical in the amount of 25 lb/acre. After 5 days, the severity of pustule formation was rated on a scale of 0 (no inhibition) to 10 (complete inhibition). See Table II for the results of these tests.

The same procedure was followed for secondary screening except lower concentrations of each chemical were employed and the spraying and drenching were separated. See Table II for the results of the secondary screening.

TABLE II

| | FUNGICIDAL ACTIVITY AGAINST CUCUMBER ANTHRACNOSE | | | | | | |
|---|---|---|---|---|---|---|---|
| | Primary Screening | Secondary Screening | | | | | |
| Compound | 25 lb/acre drench & 260 ppm spray | 12.5 lb/acre drench | 6.3 lb/acre drench | 3.2 lb/acre drench | 130 ppm spray | 65 ppm spray | 33 ppm spray |
| Example 1 | 10 | 0 | 0 | 0 | 4 | 4 | 6 |
| Example 2 | 8 | 6 | 6 | 2 | 10 | 10 | 10 |

What is claimed is:

1. A compound of the formula:

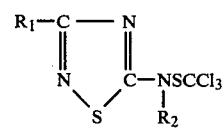

wherein $R_1$ is $CCl_3$ or $CF_3$; and $R_2$ is hudrogen, a lower alkyl having 1 to 4 carbon atoms, phenyl and substituted phenyl wherein said substituents on said phenyl group are lower alkyl having 1 to 4 carbon atoms, lower alkoxy having 1 to 4 carbon atoms, amino, nitro, halo and mixtures thereof.

2. The compound of claim 1 wherein $R_1$ is $CCl_3$.

3. The compound of claim 2 wherein $R_1$ is hudrogen.

4. The compound of claim 2 wherein $R_2$ is a lower alkyl having 1 to 4 carbon atoms.

5. The compound of claim 4 wherein said lower alkyl is methyl.

* * * * *

UNITED STATES PATENT AND TRADEMARK OFFICE
CERTIFICATE OF CORRECTION

PATENT NO. : 4,254,265

DATED : March 3, 1981

INVENTOR(S) : Walter A. Gay and Elizabeth A. Twohig

It is certified that error appears in the above-identified patent and that said Letters Patent are hereby corrected as shown below:

In column 1, line 18, "fugicides" should be --fungicides--.

In column 1, line 41, "have to 4" should read --having 1 to 4--.

In column 1, line 50, "trichllorome-" should be --trichlorome- --.

In column 2, line 2 "5amino" should be --5-amino--.

In column 2, line 3, "5methylamino" should be --5-methylamino--.

In column 2, line 5, "3-trifluror" should be --3-trifluoro--.

In column 2, line 6, "1,2,4-thiadiazol" (first occurrence) should be --1,2,4-thiadiazole--.

In column 2, line 7, "3trichloromethyl" should be --3-trichloromethyl--.

In column 2, line 8, "5methylamino" should be --5-methylamino--.

In column 2, line 8, "1,2,3-" should be --1,2,4- --.

In column 2, line 16, "thiadiaxole" should be --thiadiazole--.

In column 2, line 45, "my" should be --may--.

In column 2, line 54, "3trichloromethylthioamino" should be --3-trichloromethylthioamino--.

In column 2, line 59, "2,4dichlorophenyl" should be --2,4-dichlorophenyl--.

UNITED STATES PATENT AND TRADEMARK OFFICE
CERTIFICATE OF CORRECTION

PATENT NO. : 4,254,265
DATED : March 3, 1981
INVENTOR(S) : Walter A. Gay and Elizabeth A. Twohig It is certified that error appears in the above-identified patent and that said Letters Patent are hereby corrected as shown below:

In column 3, line 46, "dispersng" should be --dispersing--.

In column 3, line 46, ", for example." should be --, for example,--.

In column 4, line 9, "ingrediens" should be --ingredients--.

In column 4, line 12, "thse" should be --these--.

In column 4, line 30, the heading of EXAMPLE 1, "1,2,4Thiadiazole" should be --1,2,4-Thiadiazole--.

In column 4, line 38, "evaporatd" should be --evaporated--.

In column 4, line 40, "filered" should be --filtered--.

In column 4, line 51, "equpped" should be --equipped--.

In column 4, line 67, "55.50%," should be --55.50%;--.

In column 5, line 14, the beginning of the paragraph, "a uniform" should be --A uniform--.

In column 5, line 15, "as first prepared" should be --was first prepared--.

In column 5, line 17, "TRITON Z-" should be --TRITON X- --.

In column 5, line 52, "plans" should be --plants--.

UNITED STATES PATENT AND TRADEMARK OFFICE
CERTIFICATE OF CORRECTION

PATENT NO. : 4,254,265

DATED : March 3, 1981

INVENTOR(S) : Walter A. Gay and Elizabeth A. Twohig

It is certified that error appears in the above-identified patent and that said Letters Patent are hereby corrected as shown below:

In column 5, line 57, "foe" should be --for--.

In column 6, line 1, "resuls" should be --results--.

In column 6, line 52, Claim 1, "hudrogen" should be --hydrogen--.

In column 6, line 59, Claim 3, "hudrogen" should be --hydrogen--.

Signed and Sealed this

Nineteenth Day of May 1981

[SEAL]

Attest:

RENE D. TEGTMEYER

Attesting Officer    Acting Commissioner of Patents and Trademarks